United States Patent [19]

Neville, Jr. et al.

[11] Patent Number: 4,500,637

[45] Date of Patent: * Feb. 19, 1985

[54] PREVENTION OF GRAFT VERSUS HOST DISEASE FOLLOWING BONE MARROW TRANSPLANTATION

[75] Inventors: David M. Neville, Jr., Bethesda, Md.; Richard J. Youle, Washington, D.C.

[73] Assignee: The United States of America as represented by the Department of Health and Human Services, Washington, D.C.

[*] Notice: The portion of the term of this patent subsequent to Nov. 16, 1999 has been disclaimed.

[21] Appl. No.: 399,257

[22] Filed: Jul. 19, 1982

[51] Int. Cl.$^3$ .................. A61K 39/00; A01N 1/02; C12N 15/00

[52] U.S. Cl. .................. 435/2; 260/112 R; 424/85; 435/29; 436/548; 436/824; 935/108; 514/2; 514/195.1

[58] Field of Search .................. 436/548, 86, 824; 424/1.1, 85, 177, 195; 260/112 R; 435/2, 7, 68, 240, 948, 29; 935/108

[56] References Cited

U.S. PATENT DOCUMENTS

| | | | |
|---|---|---|---|
| 4,340,535 | 7/1982 | Voisin et al. | 260/112 B |
| 4,356,117 | 10/1982 | Neville, Jr. et al. | 260/112 R |
| 4,359,457 | 11/1982 | Neville, Jr. et al. | 424/85 |
| 4,361,549 | 11/1982 | Kung et al. | 424/85 |
| 4,363,758 | 12/1982 | Masutto et al. | 260/112 B |
| 4,363,799 | 12/1982 | Kung et al. | 424/85 |
| 4,368,149 | 1/1983 | Masutto et al. | 260/112 B |
| 4,397,843 | 8/1983 | Neville, Jr. et al. | 424/177 |

FOREIGN PATENT DOCUMENTS

| | | | |
|---|---|---|---|
| 0074279 | 3/1983 | European Pat. Off. | 39/395 |
| 0063988 | 3/1982 | France | 39/395 |

OTHER PUBLICATIONS

Immunological Reviews, Moller, G., ed., vol. 62, (1982), (Entire vol.), Munksgaard, Copenhagen, Denmark.
Youle, R. J. et al, Semin. Infect. Dis., vol. 4, pp. 86-88, (1982).
Jansen, F. K. et al, Research Monographs in Immunology, vol. 3, pp. 229-237, (1981).
Vitetta, E. S. et al, Proc. Leukemia Marker Conference, pp. 381-395, (2-1981).
Le Bien, T. W. et al, J. Immunology, vol. 125, pp. 2208-2214, (1980).
Ortaldo, J. R. et al, J. Immunology, vol. 127, pp. 2401-2409, (1981).
Dokhelar, M. C. et al, Transplantation, vol. 31, p. 61A, (1981).
Haynes, B. F., Immunological Reviews, vol. 57, pp. 127-161, (1981).
Reinherz, E. J. et al, Cell, vol. 19, pp. 821-827, (4-1980).
Reinherz, E. J. et al, J. Immunology, vol. 123(3), pp. 1312-1317, (9-1979).
Vallera, D. A. et al, J. Experimental Medicine, vol. 155, pp. 949-954, (3-1982).
Youle, R. J. et al, J. Biol. Chem., vol. 257(4), pp. 1598-1601, (2-1982).
Gilliland et al, Proc. Natl. Acad. Sci., vol. 77, (8), pp. 4539-4543, (1980).
Jansen et al, Chem. Abstract 95(15), 126,185u, (1981).
Neville et al, Chem. Abstract 95(17), 145,343k, (1981).
Neville et al, Biochem. Soc. Transact., vol. 8(6), pp. 692-693, (1980).
Youle et al, Proc. Natl. Acad. Sci., vol. 77(9), pp. 5483-5486, (1980).
Pau, B. et al, Chem. Abstract 94(17), 132084f, (1980).
Oeltmann, T. N. et al, Arch. Bioc. Biop., vol. 209(2), pp. 362-370, (1981).
Houston, L. L., Chem. Abstract 95(25) 214896g, (1981).
Roitt, Ivan, Essential Immunology, Blackwell Scientific Publications, 1980, (Chapters 3 and 4).
Vallera et al, J. of Exp. Medicine, vol. 155, pp. 949-954, (1982).

*Primary Examiner*—Ben R. Padgett
*Assistant Examiner*—M. Moskowitz
*Attorney, Agent, or Firm*—John S. Roberts, Jr.

[57] ABSTRACT

A monoclonal antibody known as TA-1 directed against human T-cells is covalently linked to the toxin ricin and used to treat human donor bone marrow before the marrow is infused into a human recipient.

2 Claims, 1 Drawing Figure

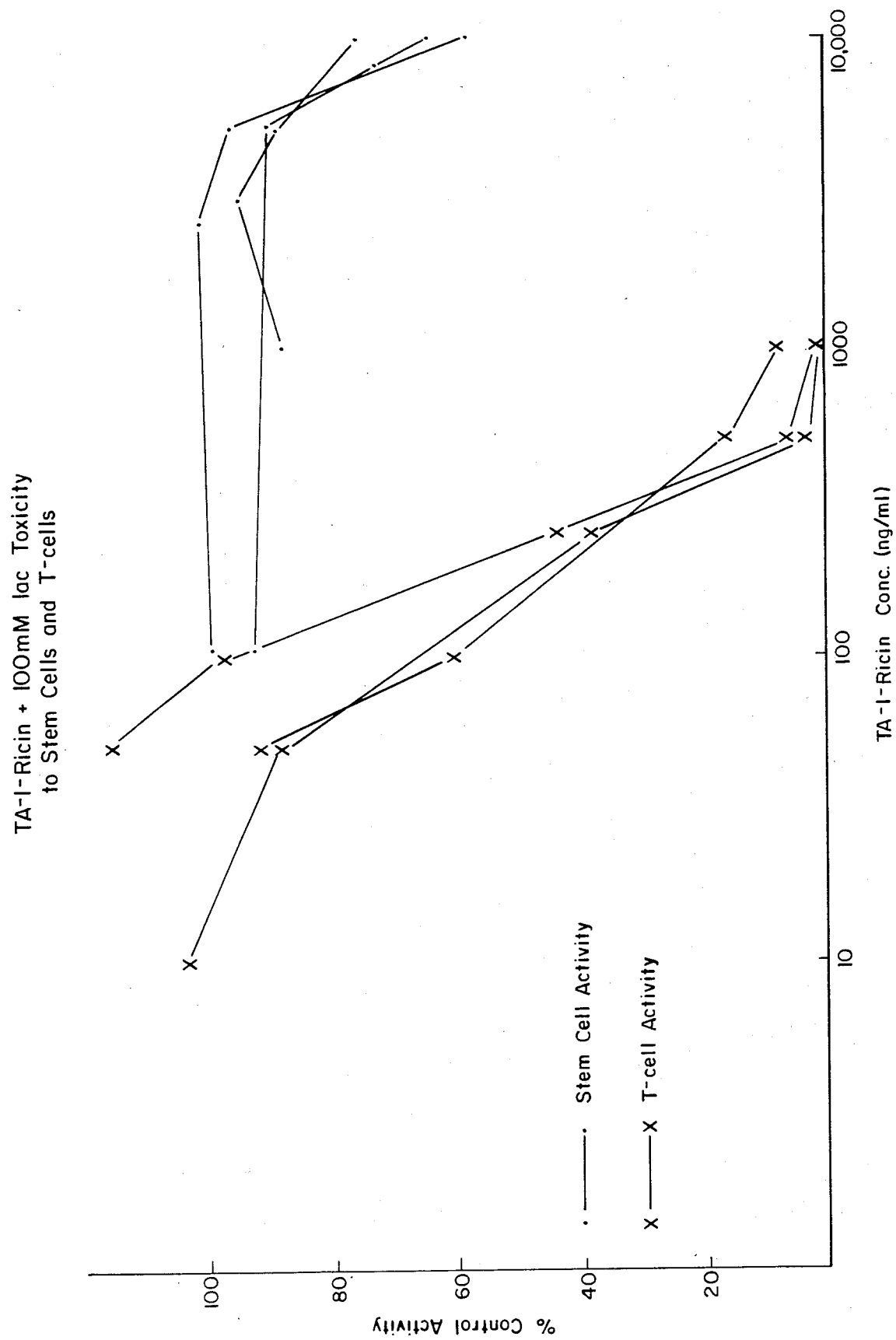

PREVENTION OF GRAFT VERSUS HOST DISEASE FOLLOWING BONE MARROW TRANSPLANTATION

GENERAL BACKGROUND

Graft-versus-host disease occurs in patients with aplastic anemia, leukemia, or other diseases who have received bone marrow transplants from non-identical donors. A major impediment to successful bone marrow transplantation is the presence of immunocompetent T lymphocytes in the donor graft which lead to the development of graft-versus-host disease (GVHD). GVHD frequently results in high morbidity and death. T-cells in the donor marrow react against the host and cause the GVHD. The problem in the past has been that elimination of the T-cells in order to prevent the disease has also produced damage to the bone marrow stem cells. Previous attempts at controlling graft-versus-host disease has centered on the use of complement plus antibody to kill the T-cells in bone marrow. However, complement has been shown to be not suitable for clinical use since it is difficult to standardize and is frequently toxic to human bone marrow stem cells. Antibody by itself, that is, without the complement, is not toxic enough to prevent GVHD.

The preliminary experiments, conducted on mice, illustrated that GVHD could be substantially prevented (anti-Thy 1.1) by binding the toxin ricin to monoclonal antibody anti-Thy 1.1 or anti-Thy 1.2. These experiments produced an assortment of moieties which prevented GVHD in mice. Some use anti-Thy 1.1 or anti-Thy 1.2 with intact ricin, others with the A chain or B chain of ricin, and others with ricin A chain followed by separate treatment with ricin B chain. In each case, the problem was the same—transporting a toxic amount of ricin across the cell wall and into the cytosol compartment where protein is made. These experiments showed (on mice) that an efficient pathway involved the application of ricin linked to anti-Thy 1.1 or anti-Thy 1.2 in a medium containing excess lactose, or ricin A chain linked to anti-Thy 1.1 plus an excess of ricin B chain added separately. (Neville and Youle, Ser. No. 350,222 and Ser. No. 350,223, both filed Feb. 19, 1982).

The application of these experiments to humans, however, is not clear-cut, thus providing the substance of this application. Humans require a different monoclonal antibody directed toward T-cells; however, such antibody must have sufficient affinity and receptor sites to efficiently direct the toxin to the cytosol compartment. The T-cell specific reagent preferred, but not limited thereby, is TA-1. Like Thy 1.1 and Thy 1.2, TA-1 is a well-known and easily produced monoclonal antibody and is commercially available from Hybritech, LaJolla, Calif. (Roitt, I., *Essential Immunology*, Blackwell Scientific Publications, 1980, Chapters 3 and 4). Human bone marrow is removed from the donor, incubated with TA-1-ricin, and placed into the human irradiated patient.

Ser. No. 186,735 (filed Sept. 30, 1980), now allowed, teaches the use of Thy 1.2-ricin on murine lymphoma cancer and is hereby incorporated by reference.

The present application teaches a human T-cell specific hybrid protein which selectively kills T-cells in human bone marrow samples without damaging the bone marrow stem cells.

UTILITY STATEMENT

TA-1 monoclonal antibody-ricin is used to eliminate T-cells from human bone marrow grafts across major histocompatibility barriers and thus prevents graft-versus-host disease (GVHD). The hybrid protein, TA-1-ricin, enters and kills cells which express the T-lymphocyte antigen. Elimination of the T-cells can be conducted without damaging the bone marrow stem cells, thus preventing the disease without killing the human stem cells necessary to repopulate the marrow in a bone marrow transplant recipient. This reagent is particularly useful in the treatment of patients with aplastic anemia or leukemia who receive bone marrow transplants. The reagent will permit bone marrow transplantation even when HLA matched siblings are unavailable as donors. The reagent is useful in any condition requiring bone marrow transplantation such as cancerous infiltration of the bone marrow, any life threatening autoimmune diseases (such as lupus erythematosus or multiple sclerosis), or organ transplantations which are commonly rejected (for example, heart transplantations). In the latter case the donor must supply both the needed organ and the bone marrow.

PRIOR ART STATEMENT

Vallera, Daniel A., Richard J. Youle, David M. Neville, Jr., and John H. Kersey, *Journal of Experimental Medicine*, Vol. 155, March 1982, pp 949–954.

Ser. No. 186,735, filed Sept. 30, 1980, Neville and Youle, now U.S. Pat. No. 4,359,457.

Ser. No. 350,222, filed Feb. 19, 1982, Neville and Youle

Ser. No. 350,223, filed Feb. 19, 1982, Neville and Youle, now U.S. Pat. No. 4,440,747.

DESCRIPTION OF THE DRAWING

The drawing shows the comparison of the toxic effect of TA-1-ricin on human bone marrow stem cells and T-cells.

SPECIFIC DESCRIPTION OF THE INVENTION

In the synthesis of anti-human-T-cell-ricin hybrid, anti-human-T-cell monoclonal IgG (TA-1) is covalently linked to ricin. TA-1 antibody, 0.25 ml at 2.6 mg/ml in 20 mM Tris-Cl pH 7.6 is mixed with 25 λ of 1 M DTT and incubated at room temperature for 30 min. The DTT is then removed by G25F gel filtration. Ricin D 0.48 ml at 10.6 mg/ml is mixed with 17 λ of MBS solution (1.5 mg of m-Maleimidobenzoyl-N-hydroxysuccinimide ester in 0.4 ml dimethyl formamide) and incubated 30 min. at room temperature. The DTT free TA-1 and MBS-ricin are then mixed and incubated 3 hrs. at room temperature. Then 20 λ of 0.2M N-ethylmaleimide is added and the hybrid is purified as previously described (Youle, R. J. and D. M. Neville, Jr., *Proc. Natl. Academy Sci., USA*, Vol. 77, pp 5483–5486, 1980.

The method used for the actual treatment of human donor bone marrow is as follows. The bone marrow is removed from the human donor, treated in vitro with TA-1-ricin under excess extracellular lactose conditions, and then infused into the irradiated recipient.

EXAMPLE

The TA-1-ricin hybrid was assayed for its effect on human T-cells and human stem cells. In vitro, the hybrid eliminated T-cells at concentrations 50-fold lower than concentrations to kill stem cells (see FIG. 1).

Procedure:

1. Add 1000 ng TA-1 ricin/ml and lactose 0.1M to bone marrow (BM) cells in 500 cc bottle. Then aliquot 40 cc BM cells into 50 cc conical polystyrene tubes. 40 cc PBMs was treated in an identical manner.

2. The 3 sets of tubes were incubated:
   (a) BM TA-1-ricin
   (b) BM $I^{125}$-TA-1 ricin
   (c) PBMs TA-1 ricin two hours at 37° C. with gentle swirling.

3. After incubation, cells were wash treated 2× with PBS with 1% HA+15 mM lactose and used as follows:

(a) BM with TA-1 ricin: washed and pooled 2× in normal saline 1% HSA. After 2nd wash, pooled BM pellets in 1 tube. Resuspended in 50 cc PBS. Take aliquot for in vitro experiments (viability studies and CFU-c) and infused the rest.

(b) BM with $I^{125}$-TA-1 ricin: Checked the amount of ricin to be injected.

(c) PBMs with TA-1 ricin: Adjusted to proper concentration.

(d) Collected $3 \times 10^8$ nucleated cells/kg body weight. Approximate yield = $20 \times 10^6$ mononuclear cells/ml. $20 \times 10^6$ cells/ml × 1000 ml = $20 \times 10^9$ cells in 1 liter. Recovery from Hetastarch and Ficoll = 25%.

$0.25 \times 20 \times 10^9$ cells = $5 \times 10^9$ cells total Results: See the FIGURE.

We claim:

1. The method for treating graft versus host disease in humans comprising covalently linking an antibody TA:1 which specifically binds to human T:lymphocytes to intact ricin toxin in order to form a human T-cell specific hybrid; incubating said hybrid with human donor bone marrow cells prior to injecting said bone marrow cells into irradiated recipients, said TA:1 antibody is an antibody of the IgG2 subclass exhibiting an affinity for human T-cells of $10^{-9}M^{-1}$.

2. A method of eliminating T-cells from human bone marrow grafts by up to 98% consisting of covalently linking TA:1 monoclonal antibody to ricin toxin, incubating TA:1: ricin with human bone marrow cells and adding at least 100 mM lactose, said TA:1:ricin is a conjugate of ricin toxin covalently bound to a monoclonal antibody which specifically binds to human T:lymphocytes.

* * * * *